(12) United States Patent
Bosnjakovic

(10) Patent No.: US 6,194,728 B1
(45) Date of Patent: Feb. 27, 2001

(54) IMAGING DETECTOR FOR UNIVERSAL NUCLEAR MEDICINE IMAGER

(75) Inventor: Vladimir Bosnjakovic, Belgrade (YU)

(73) Assignee: ADAC Laboratories, Milpitas, CA (US)

( * ) Notice: Subject to any disclaimer, the term of this patent is extended or adjusted under 35 U.S.C. 154(b) by 0 days.

(21) Appl. No.: 09/165,160

(22) Filed: Oct. 1, 1998

Related U.S. Application Data

(63) Continuation of application No. PCT/US97/07714, filed on May 5, 1997.

(51) Int. Cl.$^7$ ................................. G01T 1/20; G01T 7/00
(52) U.S. Cl. ............................... 250/370.11; 250/363.02; 250/363.03; 250/366; 250/369
(58) Field of Search .......................... 250/370.11, 363.02, 250/363.03, 366, 369, 393

(56) References Cited

U.S. PATENT DOCUMENTS

| | | |
|---|---|---|
| 3,011,057 | 11/1961 | Anger . |
| 3,745,345 | 7/1973 | Muehllehner . |
| 3,921,000 | 11/1975 | Muehllehner . |
| 3,943,336 | 3/1976 | Dillard et al. . |
| 4,057,725 | 11/1977 | Wagner . |

(List continued on next page.)

OTHER PUBLICATIONS

Hal O. Anger, "Scintillation Camera", The Review of Scientific Instruments, vol. 29, No. 1, Jan., 1958, pp. 27–33.
Hal O. Anger, "Gamma–Ray and Positron Scintillation Camera", Nucleonics, vol. 21, No. 10, Oct. 1963, pp. 56–59.
Hal O. Anger and Donald H. Davis, "Gamma–Ray Detection Efficiency and Image Resolution in Sodium Iodide", The Review of Scientific Instruments, vol. 35, No. 6, Jun. 1964, pp. 693–697.
Hal O. Anger, "Sensitivity, Resolution and Linearity of the Scintillation Camera", IEEE Transaction Nuclear Science, vol. NS–13, No. 3, Jun. 1966, pp. 380–392.

(List continued on next page.)

Primary Examiner—Constantine Hannaher
Assistant Examiner—Otilia Gabor
(74) Attorney, Agent, or Firm—Blakely, Sokoloff, Taylor & Zafman

(57) ABSTRACT

A universal nuclear medicine imager (UNMI) enables planar, SPECT and PET studies. The UNMI is a "position sensitive" type of detector which has a relatively thick (e.g., ⅝ in.) NaI(Tl) crystal optically divided by a thin non-scintillating material into two half-thicknesses of ⅜ in. each. The UNMI detector uses a light collimator system to enable a depth of interaction (DOI) determination in addition to a two-dimensional location of gamma photons in the half-thicknesses of the crystal. The system includes a combination of a scintillating, optically more dense material with a non-scintillating, optically less dense material and uses the light refraction reflection law with PM tubes and coincidence circuits. For obtaining the optimal spatial resolution in planar and SPECT studies, a known DOI enables the use of only the lower ⅜ in. of the crystal (energies up to 150 KeV) or both of the half-thicknesses for medium energies (250, 360 KeV), with the resolution in each being corrected by use of digital filters. In PET detection of 511 KeV energies, a known DOI improves the resolution by correcting for parallax error in addition to the use of an adequately thick crystal.

19 Claims, 6 Drawing Sheets

U.S. PATENT DOCUMENTS

| | | | |
|---|---|---|---|
| 4,272,678 | * | 6/1981 | Lange ............................. 250/363.02 |
| 4,394,576 | * | 7/1983 | Tanaka et al. ...................... 250/366 |
| 4,675,526 | | 6/1987 | Rogers et al. . |
| 4,677,299 | | 6/1987 | Wong . |
| 4,700,074 | | 10/1987 | Bosnjakovic . |
| 4,733,083 | * | 3/1988 | Wong ............................. 250/363.03 |
| 4,843,245 | | 6/1989 | Lecomte . |
| 5,122,667 | | 6/1992 | Thompson . |
| 5,349,191 | | 9/1994 | Rogers . |
| 5,585,637 | * | 12/1996 | Bertelsen et al. ............... 250/363.03 |
| 5,616,924 | * | 4/1997 | Petrillo ................................. 250/368 |

OTHER PUBLICATIONS

G. Muehllehner, et al., "Correction for Field Nonuniformity in Scintillation Cameras Through Removal of Spatial Distortion", The Journal of Nuclear Medicine, vol. 21, No. 8, Aug. 1980, pp. 771–776.

G. Muehllehner, et al., "Performance Parameters of a Positron Imaging Camera", IEEE Transaction on Nuclear Science, vol. NS–23, No. 1, Feb., 1976, pp. 528–537.

Michael E. Phelps, et al., "Application of Annihilation Coincidence Detection to Transaxial Reconstruction Tomography" Journal of Nuclear Medicine, vol. 16, No. 3, Mar. 1975, pp. 210–224.

Michael E. Phelps, et al., Design Considerations for a Positron Emission Transaxial Tomograph (PETT III), IEEE Transations on Nuclear Medicine, vol. NS–23, No. 1, Feb. 1976, pp. 516–522.

Z.H. Cho and M.R. Farukhi, "Bismuth Germanate as a Potential Scintillatio Dectector in Positron Cameras", Journal of Nuclear Medicine, vol. 18, No. 8, Aug. 1977, pp. 840–844.

Michael E. Phelps, et al., "ECAT: A New Computerized Tomographic Imaging System for Positron–Emitting Radiopharmaceuticals", The Journal of Nuclear Medicine, vol. 19, No. 6, Jun., 1978, pp. 635–647.

James A. Sorenson, Ph.D. and Michael E. Phelps, Ph.D., *Physics in Nuclear Medicine*, 1987.

J.S. Karp, et al., "Event Localization in a Continuous Scintillation Detector Using Digital Processing", *IEEE Trans. Nucl. Sci.*, vol. 33, No. 1, Feb. 1986, pp. 550–555.

J.S. Karp, et al., "Continuous–Slice PENN–PET: A Positron Tomograph with Volume Imaging Capability," *Journal of Nuclear Medicine*, vol. 31, No. 5, May 1990, pp. 617–627.

E.J. Hoffman, et al., "Dynamic, Gated and High Resolution Imaging with the ECAT III," *IEEE Trans. Nucl. Sci.*, vol. 33, No. 1, Feb. 1986, pp. 452–455.

E. J. Hoffman, et al., "Performance on a NeuroPET System Employing 2–D Modular Detectors," *Journal of Nuclear Medicine*, vol. 29, No. 5, May 1988, pp. 983–992.

G. Muehllehner et al., "PET Scanner with PET Coincidence Capability," *Journal of Nuclear Medicine*, Jun. 14, 1998, pp. 70P.

* cited by examiner

IMAGING DETECTOR FOR UNIVERSAL NUCLEAR MEDICINE IMAGER

This application is a continuation, under 35 U.S.C. § 120, of International Patent application No. PCT/US97/07714, filed on May 5, 1997 under the Patent Cooperation Treaty (PCT), which claims the benefit of Yugoslav patent application No. P298/96, filed on May 17, 1996.

FIELD OF THE INVENTION

The present invention pertains to the field of medical imaging equipment. More particularly, the present invention relates to a system for performing both planar studies as well as single-photon emission and positron emission tomography.

BACKGROUND OF THE INVENTION

There are two distinctive types of imaging systems in contemporary nuclear medicine. One type is represented by the gamma scintillation cameras (GSCs), the so-called "position sensitive" continuous-area detectors, and the other one by Positron Emission Tomography (PET) scanners. The first type deals with the single photon gamma emitters enabling planar static and dynamic studies as well as Single Photon Emission Computed Tomography (SPECT), while the second type enables tomographic imaging of the positron emitters, i.e., PET studies. Both techniques enable direct imaging of biochemical processes "in vivo" (especially, the PET technique) and the study of physiological processes and dysfunctions in a quantitative manner. However, imaging systems for both types of techniques are rather expensive. The costs involved for these systems have greatly contributed to the overall expenditures for contemporary high technology medicine, which is a serious problem even in the most developed countries (e.g., U.S.A., Japan, United Kingdom, Germany, and France). Besides the commercial problem, there is a scientific problem: that of enabling simultaneous application (in the same person) in a short sequence of single photon gamma and positron emitters.

Thus far, it seems that there has been no satisfactory solution for a unique design to image both single photon and positron emitters. Contemporary PET scanners with their circumference arrangements of BGO crystals (efficient absorbers of high photon energies of 511 KeV emanating from positron emitters), i.e., of small opposing detectors connected with coincidence electronics, are designed to detect exclusively the positron emitters in a tomography mode. Position sensitive area detectors of the GSC type are made with the thin NaI(Tl) crystals for optimal imaging detection of the low energy single photon gamma emitters; here, optimal imaging detection assumes an optimal spatial resolution for energies up to 150 KeV, with a shortage of the detection efficiency for medium and higher energies of single photon gamma emitters (250 and 360 KeV) being significantly reduced. Such a reduced efficiency makes the detection of high energy photon emissions, such as the ones of 511 KeV from positron emitters, difficult or impossible. There is a design of a system made of opposing position sensitive area detectors in coincidence mode fitted with thick (1 inch (in.) for increased efficiency) NaI(Tl) crystals, to be used only for tomographic detection of positron emitters (due to the intolerantly worse spatial resolution for lower energies of single photon emitters). The fact, however, that this is also an imager aimed at serving PET exclusively, as well as that in such a system, the optimal spatial resolution for PET has not still been achieved due to the inherent "parallax" error, emphasizes and indicates the need for an imaging system which solves the above mentioned problems.

References which may be of interest include the following, which concern the design of position sensitive GSC type detectors:

U.S. Pat. Nos: 3,011,057; 3,745,345; 3,921,000; 3,943, 336; 4,057,725; 4,700,074;

H. O. Anger: Rev. Sci. Inst., 29, 27, (1958);

H. O. Anger: Nucleonics, 21, 10, 56, (1963);

H. O. Anger and D. H. Davis Rev. Sci Inst., 35, 6, 693, (1964);

H. O. Anger: IEEE Trans. Nucl. Sci., 13, 3, 380, (1966); and

G. Muehllehner, et al.: J. Nucl. Med., 21, 771, (1980).

In addition, the following references concern the design of PET scanners based on position sensitive imaging detectors fitted with thick (e.g., 1 in.) NaI(Tli) crystals:

G. Muehllehner, et al.: IEEE Trans. Nucl. Sci., 23, 1, 528, (1976);

J. S. Karp, et al.: IEEE Trans. Nucl. Sci., 33, 1, 550, (1986); and

J. S. Karp, et al.: J. Nucl. Med., 31, 617, (1990).

Finally, the following references concern the design of "classic" PET scanners, mostly fitted with a circumference arrangement of BGO crystals:

M. E. Phelps, et al.: J. Nucl. Med.; 16, 210, (1975);

M. E. Phelps, et al.: IEEE Trans. Nucl. Sci., 23, 516, (1976);

Z. H. Cho, et al.: J. Nucl. Med., 18, 840, (1977);

M. E. Phelps, et al.: J. Nucl. Med., 19, 635, (1978);

E. J. Hoffman, et al.: IEEE Trans. Nucl. Sci., 33, 1, 452, (1986);

E. J. Hoffman, et al.: J. Nucl. Med., 3, 29, 983, (1988).

J. A. Sorenson and M. E. Phelps: Physics in Nuclear Medicine Sec. Edit., Saunders (1987).

SUMMARY OF THE INVENTION

The present invention includes a radiation detector comprising a plurality of scintillation crystal layers and a light collimator system optically coupled to the scintillation crystal layers for determining a depth of interaction associated with a scintillation event. Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
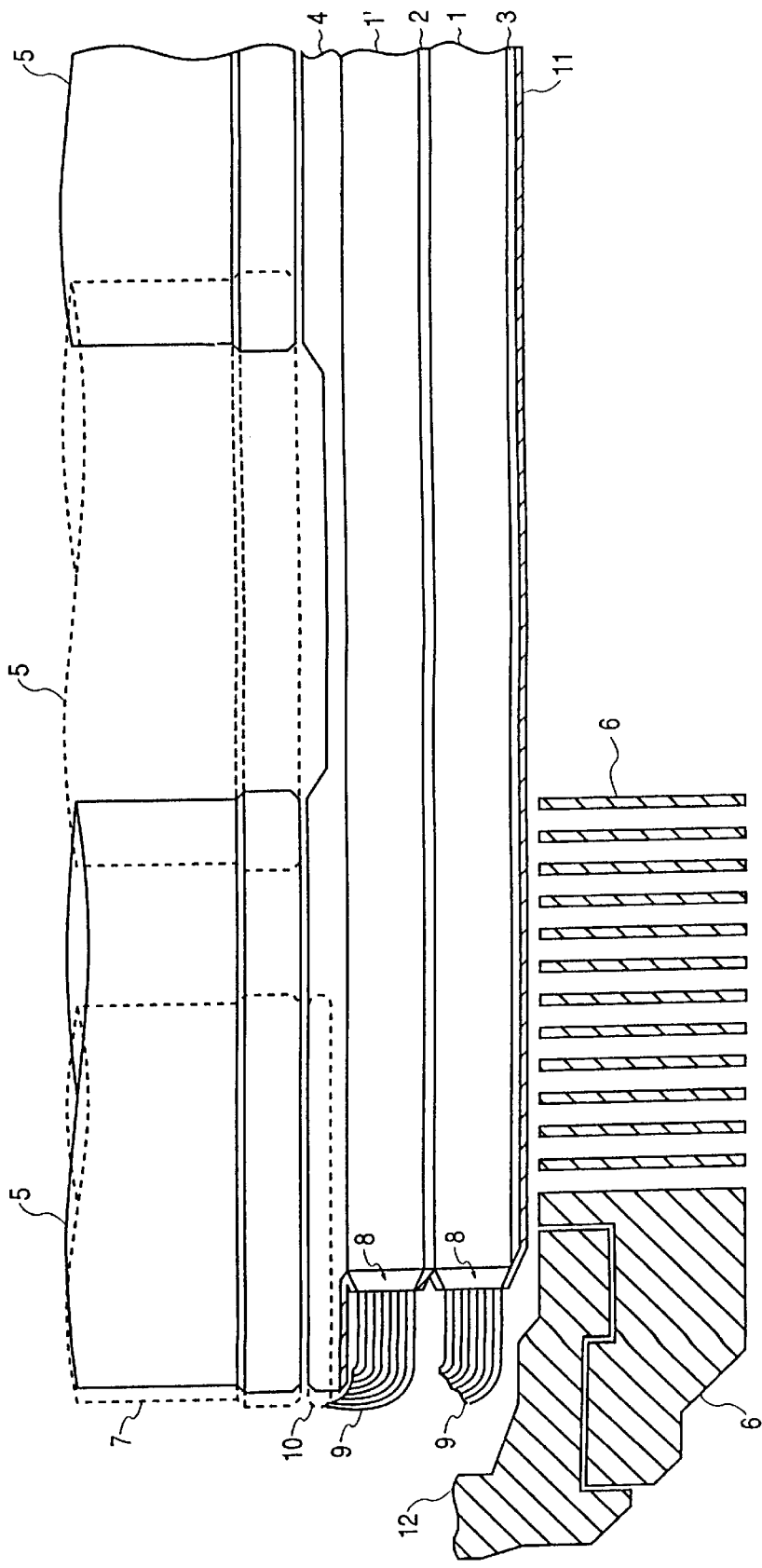
FIG. 1 illustrates a vertical cross-section of a Universal Nuclear Medicine Imager (UNMI).

A universal nuclear medicine imaging detector is described. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to facilitate description of the present invention.

The technical problem to be solved by the present invention is the design of a universal imaging detector for nuclear medicine which incorporates one or more detectors, referred to herein as the "Universal Nuclear Medicine Imager" (UNMI), which enable both the performance of planar studies (static, with the adequate spatial resolution and fast dynamic—metabolic with adequate temporal resolution), and optimal emission tomography studies with single photon emitters ("SPECT") and positron emitters ("PET"). The solution of the technical problem is to remove the shortage of GSCs to detect efficiently higher single photon and positron gamma energies, as well as the shortage of PET scanners to perform planar and SPECT studies with single photon gamma emitters; thus, the solution assumes a new design of a detector for the universal nuclear medicine imager (UNMI).

A conclusion arising from the "Background of the Invention" (above) is that a UNMI system might and should be based on position sensitive area imaging detectors, since various types of these detectors with different NaI(TI) crystal thicknesses were used for imaging both single photon and positron emitters. On the other hand, the design of a typical "classical" PET scanner could not fulfill the requirements of SPECT and, in particular, of planar studies. In order to satisfy the requirements of planar—SPECT and PET systems, UNMI design has to be technically solved in such a way to have a thick NaI(TI) crystal (for the efficient detection of high photon energies in PET) enabling it to provide a satisfactory spatial resolution to image the low single-photon energies (in planar and SPECT studies).

A solution for such a technical problem lies in the possibility to determine exactly the "third dimension—location" of an event, i.e., the depth of interaction (DOI) of a gamma photon of any energy in a thick, large NaI(TI) scintillation crystal. A precisely known DOI of a gamma photon in a thick crystal would provide the means for employment of the adequate correction schemes and principles for a distorted spatial resolution, both in planar—SPECT and PET studies.

In principle, the solution of the present invention concerns a DOI determination in any kind of a scintillation crystal of lower or higher density, but in this description, only the DOI determination in a thick NaI(TI) crystal will be considered. Good characteristics of NaI(TI) crystal in comparison with certain others (e.g., BGO, CsF, BaF, CsI, GSO, and the latest LSO) are: the best yield of scintillation light, negligible attenuation of light in the crystal, excellent energy resolution (enabling an efficient removal of Compton scatter), ability to grow large crystals (needed for GSC "large field of view" type of detectors) thus obtaining a large acceptance angle in configuration of large "position sensitive" area detectors (important for the efficient three-dimensional (3D) PET detection), and finally, but not least important, that it is the most widely used and applied crystal with broadly elaborated technology of production making it convenient for its fabrication in various shapes and sizes, being the cheapest one at the same time.

The solution of the technical problem is achieved by an innovation in designing the imaging "position sensitive" detectors, i.e., by the addition of a new, original design of a "light collimators" (LC) system. The LC system (which includes its own electronics) in combination with a thick NaI(TI) crystal and standard electronics for the two-dimensional (2D) location of an interaction of gamma photon (IGP), enables the determination of the DOI of gamma photons in such a crystal and detector system. This determination is enabled by dividing the unique whole of the crystal (as existing in conventional standard GSCs) into isolated DOI layers by inserting a non-scintillating but light-transparent material of different refractive-reflective characteristics, as compared to the NaI, in a thick crystal; as a result, the inserted material does not stop the gamma photons which are normally absorbed in various depths of scintillation crystal according to the exponential law probability.

The new system of UNMI detector is presented in FIG. 1 in a vertical cross-section by a proportional drawing of the parts. The system is presented in a simple embodiment, being a highly acceptable one from the commercial and performance predictability aspects, i.e., having only two DOI layers of ⅜ inch (in.) thickness each (which is the sole total thickness of NaI crystal in standard contemporary GSCs) within the total ⅝ in. thickness of NaI(TI) crystal. The cross-section in FIG. 1 through a part of the UNMI detector shows the thick NaI(TI) crystal separated in two layers (1, 1'), each being ⅜ in. thick, by a thin layer of the internal part (2) of LC system, and delineated by the remaining internal parts (3, 4) of LC system, which are made of quartz glass $SiO_2$); part-layer (4) of the LC is at the same time a part of a light guide coupling the NaI and a conventional array of photomultiplier (PM) tubes (5).

The cross-section of FIG. 1 also shows the following additional parts of detector and electronics: a lead collimator (6) of gamma photons; a conventional array (5) of PM tubes 3 in. in diameter, which in "position sensitive" detectors determine a 2D, (x,y) location of an IGP; a UNMI-original array of PM tubes (7) that are 2 in. in diameter, which collect the light from each of the DOI layers (half-thicknesses) of the crystal (1, 1'), by means of the corresponding external LCs (8) via fiber optic quartz light guides (9) and a light guide (10), which is also made of $SiO_2$ for coupling fiber optic light guides (9) to the UNMI PM tubes (7); an aluminum hermetic cage (11) encompassing the crystal, the external LCs, and a part of the light guide; and, a part (12) of the detector housing made conventionally of an adequate protective thickness of lead and steel construction elements.

As pointed out above, the specificity and characteristics of the UNMI design lie in the LC system in block with a thick crystal and the additional UNMI PM tubes array and electronics system, which together with the conventional (x,y) locating electronics (and PM tubes array), determine the DOI of a gamma photon event and a two-demensional location in that particular DOI. The LC system itself (shown in FIG. 1) consists of two parts, an internal part (2,3,4) and external part (8), and it is made of quartz glass $SiO_2$). The internal part of the LC is the one which forms the DOI layers of NaI scintillator (1, 1') of the predetermined desired thicknesses (in this case, the two layers of NaI of 3/8 in. thickness each) within a thick NaI(Tl) crystal, formed in a way that the scintillator layers are separated, and the lowest layer (1) is outlined by the thin layers (0.03 in., or 0.762 mm, of thickness) of non-scintillating material-quartz glass (2, 3). Optical couplings of the scintillating and non-scintillating materials have smooth, polished surfaces for enabling (partial) reflection of the light within the DOI layers of NaI, depending on the ratio of refraction indices of the NaI and $SiO_2$. The external surface of the lowest outlining thin quartz layer (3) is diffuse reflectively painted (and/or scratched) in order to help the collection of light by the conventional, "position sensitive" PM tubes array. Thus, the "channeled" scintillation light within each of the scintillator DOI layers is "collected" on the side of a thick, large NaI crystal by means of the corresponding external LCs (8), which fit in height the DOI layer thicknesses of NaI scintillator.

The external LCs differ in design, depending on the number and thicknesses of DOI layers in the crystal. The external LCs are coupled to the fiber optic light guides (9), and these are, by means of the quartz glass layer(s) (10), optically coupled to the specific UNMI (array of) PM tubes (7) (and additional electronics) for determining the DOI of gamma photons. The blocks of the external LC system are mounted on the lateral (vertical) sides of a thick NaI(Tl) crystal, of a "sandwich" type, serving at the same time as a part of a hermetic "cage" for the hygroscopic NaI scintillator, instead of a conventional part made of aluminum; the rest of the "cage", protecting the lower part of the crystal towards the lead collimator and covering the parts of light guides and external LCs, is made of aluminum (11).

Figure 2:
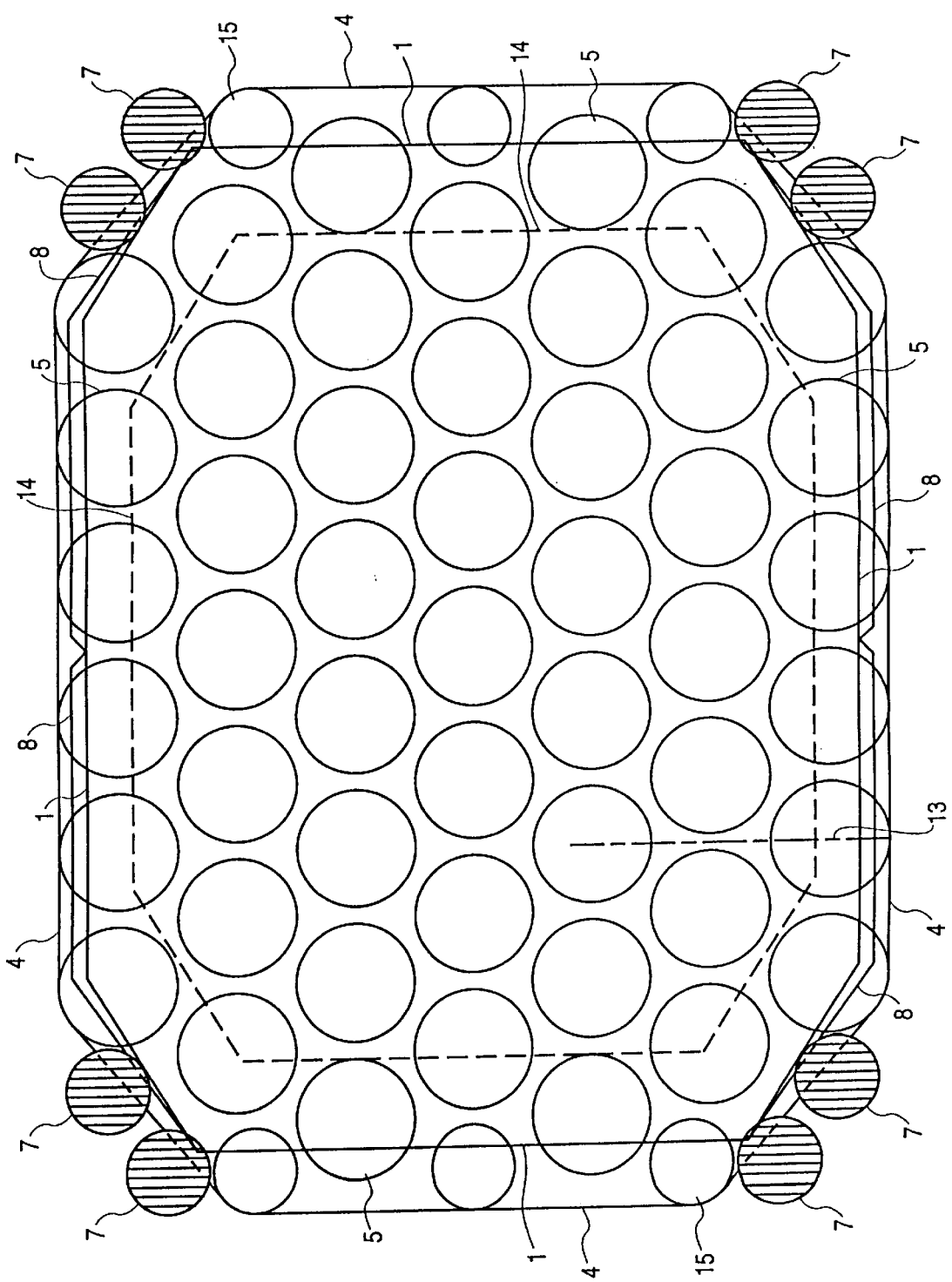
FIG. 2 illustrates a horizontal cross-section of a Universal Nuclear Medicine Imager (UNMI) with two depth of interaction (DOI) layers.

FIG. 2 illustrates a horizontal cross-section through the UNMI detector of FIG. 1, with two DOI layers in a 6/8 in. thick NaI crystal (each layer of 3/8 in. thickness). Dashed lines (13) show one of the possible locations of the vertical cross-section, given in FIG. 1. In FIG. 2, the following elements (in horizontal cross-section) correspond in shape and dimension to one of the commercial types of position sensitive "area" detectors, like one of the standard GSCs (most closely, to some of the GSCs made by companies such as ADAC Laboratories of Milpitas, Calif.): a large NaI(Tl) crystal (1), "rounded" at the corners, with dimensions of 25 in.×18.75 in. (63.5 cm×47.6 cm) (measures of rectangle which are not strictly specific for UNMI design can vary accordingly), and the total thickness of which is 2 in.×3/8 in., this type being 3/8 in. in commercial standard GSCs; "effective" 2D fields of view given in dashed lines as a rounded rectangle (14) with the dimensions of 20.4 in.×15 in. (51.8 cm×38.1 cm); a conventional GSC array having a total of 55 PM tubes, which in "position sensitive" detectors determine the two dimensional, (x,y) locations of IGPs, of which 49 PM tubes are of 3 in. in diameter (5), and six PM tubes are of 2 in. in diameter (15) to fill in (by their smaller dimensions and "weighing" factors), as in some of the commercial arrays, the spaces at edge parts of the crystal; light guide (4) encompassing by its dimensions the whole of the conventional array of 55 PM tubes.

Original elements in FIG. 2 characteristic of the UNMI are given in horizontal cross-section by the marked blocks of external LCs and UNMI array of PM tubes. External LCs are pasted as the blocks of two layers on each half of the longitudinal side of a rectangular thick crystal, including its rounded portions at the angles (8), too. Hence, this UNMI design has the total of four blocks, each having two layers of external LCs, making a total of eight external LCs; thus, each of the external LCs "pulls out" scintillation light from one quadrant of the scintillation crystal and from its one layer thick 3/8 in. Each of the eight external LCs is connected by a fiber optic light guide (not shown in FIG. 2) to one of the PM tubes of 2 in. in diameter from UNMI array (7). Collecting the light predominantly from one quadrant of the crystal is advantageous not only because of the shortest path of light through a rectangular crystal (least attenuation effect), but also because the external effective surface of an external LC to which an appropriately "widened" bundle of fiber optic cable has to be pasted fits the surface size (of the photocathode) of a PM tube of 2 in. in diameter used in UNMI array, to which the other "narrowed", appropriately rounded end of the bundle of fiber optic cable has to be pasted. The length of the external effective surface of a "rectangle" shaped external LC is nearly 12.6 in. and its height is 0.25 in., which makes its effective surface, $S_{1c}$, where $S_{1c} = 12.6 * 0.25 = 3.15$ $in^2$. This is close to the surface size of photocathode, $S_p$, of a PM tube of 2 in. in diameter, where $S_p = r^2 \pi = 3.14$ $in.^2$. The design details of the blocks of-external LC system (8), with theoretical explanation are discussed below.

The theoretical background of the technical solution of UNMI problem will now be discussed. The technical solution of UNMI problem is theoretically grounded on the specific effects and different penetrating power of the two crucial types of radiations which are used in scintillation detection of gamma radiation of gamma photons themselves and of the resultant light photons. In fact, the possibility to "channel" scintillation light within the crystal is used applying the refraction/reflection law of light, i.e., by inserting a material of the different refraction/reflection characteristics compared to NaI, which in turn does not diminish by its density the penetrating power of gamma photons and their distribution in a crystal. The exact "channeling" of light will provide for accurate information on the DOI of gamma photons in the crystal. In view of this concept, the theoretical background of the technical solution is based on the following known phenomena, facts and laws:

1) the exponential law of attenuation and absorption of various energies of gamma photons in various depths of scintillation crystal, as well as on cross-sections for the various effects of interactions of gamma photons (photoelectric, Compton, and on summarized "photopeak" effect) in these depths;

2) refraction and reflection of light of particular wavelengths in particular materials; and 3) conversion "yield" of quantity of light photons relative to the energy of gamma photons absorbed in NaI;

4) "quantum efficiency" of photocathodes (bialkaly) of PM tubes;

5) light distribution from various DOIs of gamma photons on both systems of PM tubes (position sensitive and UNMI) and its influence on spatial resolution of the UNMI system;

6) characteristics of NaI(Tl) as a suitable scintillator for UNMI design; and 7) characteristics of some newly produced crystals, in particular LSO, as a suitable scintillator for UNMI design.

The essential function of the internal part of LC system is to "channel" the portion of light from a scintillation event through the corresponding NaI layer to the adequate external part of LC system (and UNMI PM tubes) for the determination of the DOI of gamma photon; the rest of the portion of light from a scintillation event, depending on the "critical angle", has to be captured by the conventional position sensitive PM tubes array for the determination of the two-dimensional location of the IGP. This goal can be achieved by the illustrated UNMI "sandwich" design of NaI(Tl) crystal, where the NaI layers of particular thicknesses (in which the determination of DOI is desired) are separated by the layers of non-scintillating, light-transparent material with a different light refraction index relative to NaI, such as quartz glass ($SiO_2$). The theoretical background of this solution is given in an example shown in FIG. 3.

Figure 3:
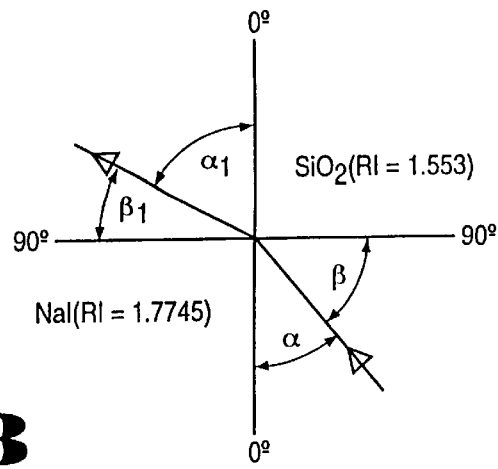
FIG. 3 is a diagram illustrating the theoretical background of the UNMI.

FIG. 3 shows that if a light photon of an angle, $\alpha$, relative to a vertical of 0°, traverses from an optically more dense medium like the NaI(Tl) crystal (with its refraction index, RI, equal to 1.7745) to an optically less dense medium like the quartz ($SiO_2$) (with its refraction index, RI, equal to 1.553) (considering sodium light of wavelength of, $\lambda$=589.3 m$\mu$), the photon turns with an angle, $\alpha_1$, from vertical, where, $\alpha_1 > \alpha$. Considering the relations of the light refraction/reflection law, it follows that a limiting angle, $\alpha$, which would enable, $\alpha_1$, to be 90° relative to a vertical, should equal: sin $\alpha$=sin 90°*(RI of $SiO_2$)/(RI of NaI)=1* (1.553/1.7745)=0.875, then $\alpha$=61.5°. The "critical" incoming angle, relative to a horizontal of 90° (which, instead of refraction of light in SiO2, would enable its reflection back to NaI), $\beta$, would then equal: $\beta$=90°−$\alpha$=28.5°. Thus, any incoming light photon with an angle less than 28.5°, relative to a horizontal (as 90°), would be reflected from $SiO_2$ and within an NaI layer "channeled" toward its lateral sides. A prerequisite for the refraction and/or reflection phenomena is that the coupling surfaces of NaI and SiO2 should be perfectly polished and "optically coupled".

Figure 4:
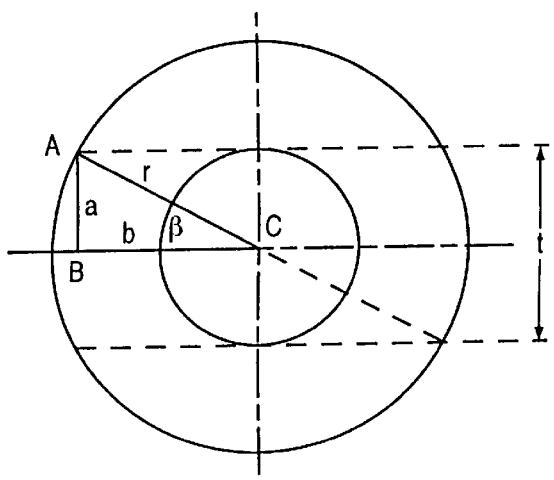
FIG. 4 is a diagram illustrating the relations existing by determining vertical geometric efficiency (VGE) factors.

Since the light photons isotropically spread out to all sides, the fractions of light photons coming to the lateral sides of the crystal could be precisely defined and determined by inserting the thin $SiO_2$ layers in NaI to "channel" them to these sides. Based on isotropic spread out, the light fractions coming to the lateral sides of the crystal can be determined considering the "geometric efficiency". FIG. 4 shows the relations existing by considering the geometric efficiency of the vertical cross-section of the design, i.e., by determining the vertical geometric efficiency (VGE) factors. If:

$\beta$="critical" angle;

C=center of the sphere of isotropic spread of light (i.e., the site of an IGP in a DOI layer of the crystal);

r=radius of the sphere;

t=thickness of the DOI layer in crystal (i.e. of the belt of sphere having this thickness (=2a); and a=cathetus of the triangle ABC (=t/2);

then, we have:

$$r = a/\sin \beta \quad (1)$$

since the surface of the sphere, Ps, is given by: Ps=4$r^2\pi$, and the surface of the belt of sphere, Pbs, is given by: Pbs=−2$\pi$t, then VGE is given by the ratio of these surfaces, i.e.:

$$VGE = 2r\pi t/4r^2\pi = t/2r = 2a/(2a/\sin \beta) = \sin \beta \quad (2)$$

Consequently, we come to the very favorable conclusion for further design considerations of UNMI concerning the number and the thicknesses of DOI layers in a thick NaI crystal, that the VGE is independent of these factors as well as of the site of IGP in a DOI layer, being only dependent on, and being the function of, the "critical" angle, , $\beta$, i.e., of its sine. For a "critical" angle, $\beta$, of 28.5°, VGE=sin (28.5°)= 0.4771=47.71%.

Figure 5:
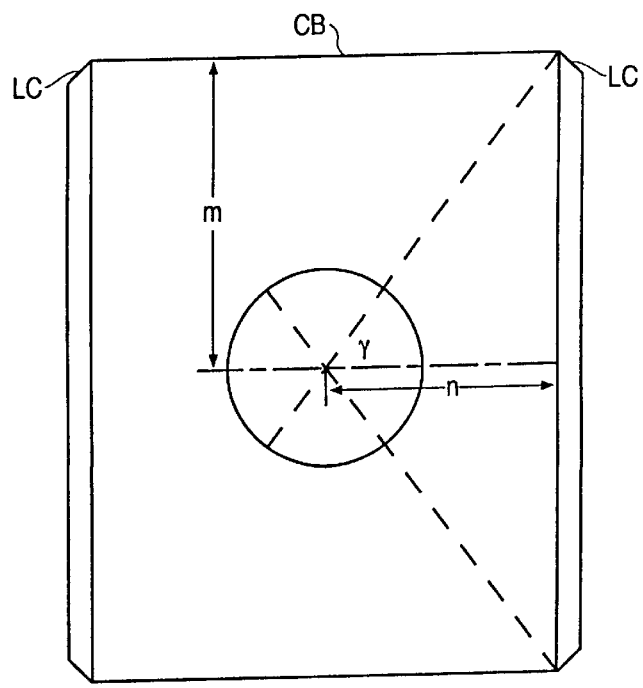
FIG. 5 is a diagram illustrating the relations concerning horizontal geometric efficiency (HGE).

FIG. 5 shows the relations concerning horizontal geometric efficiency (HGE), i.e., it shows an insight in the fraction (s) of the belt of the sphere as "seen" by the external LCs. The crystal block (CB) is schematically simplified shown as a rectangle (without rounded angles), with blocks of external LCs (LC) mounted on both longitudinal sides of the crystal block. A light emission from the geometric midpoint of the crystal is considered. From the relations shown in FIG. 5, we have:

$$m/n = tg\gamma \quad (3)$$

$$HGE = 4\gamma/360° \quad (4)$$

For dimensions of the crystal of 24.5 in.×18.0 in., and of the corresponding sizes of, half-length, m, half-width, n, and angle, $\gamma$, we have from relations (3) and (4): tg$\gamma$=12.25/9.0= 1.361; $\gamma$=53.7°; then: HGE=4*53.7/360=0.596=59.6%, coming from both, at side-length mounted external LCs (divided in 4 portions, encompassing 4$\gamma$) per DOI layer. The total geometric efficiency (TGE) per DOI layer of the crystal is then given by:

$$TGE = HGE * VGE \quad (5)$$

On the basis of the above-derived values we have: TGE=0.596*0.4771=0.2843=28.43%.

The given data indicate that about 28.43% of the total number of isotropically emitted light photons from the geometric midpoint of a DOI layer in the crystal would be "captured" by this layer. The data which would indicate whether such an efficiency might be sufficient for the intended goal (i.e. for determining the layer of DOI of gamma photon in the crystal) follow from the known conversion relations: energy of an incoming $\gamma$ photon— amount of emitted light photons—"captured" fraction of light photons (by the UNMI's LC system)—amount of ejected primary photoelectrons from photocathode(s) of the UNMI PM tube(s). It is known that in a NaI crystal (having the greatest light yield among the scintillation crystals commonly in use, which is exceptionally important for creating large area detectors, and in particular the UNMI design) a gamma photon energy of 30 electron volts (eV) produces approximately 1 light photon; i.e., a typical low energy $\gamma$ photon of 100 KeV (considering the least favorable possibility within a spectrum of the practically used gamma energies ranging from 100–500 KeV) produces 3333.33 light photons, which with a TGE of 28.43% yields about 948 light photons per DOI layer. Since contemporary PM tubes with a relatively high "quantum efficiency" of their photocathodes convert around 30% of light photons into photoelectrons, a gamma ray energy of 100 KeV would produce about 284 primary photoelectrons per DOI layer, which would enable a satisfactory discrimination from neighboring DOI layers concerning the resulting magnitude of the output signal from PM tube(s). Namely, the output from all of the PM tubes in the UNMI design which "view" one DOI layer (four UNMI PM tubes per DOI layer in the design shown in FIGS. 1 and 2) is taken to be a common one. Thus, any two-dimensional, (x,y) location of an IGP, no matter to which one of the four external LCs quadrant LCs it is near (or distant from), as summed up via the UNMI DOI-LC system provides for a similar magnitude of the output signal indicative for a particular DOI layer. This would in any case enable discrimination of any particular DOI layer from the other one(s), which is the essential function of the UNMI LC system for determining the DOI of gamma photons in a thick crystal. The conversion relations become proportionally more optimal for higher than 100 KeV gamma photon energies. The advantages of an NaI scintillator (the highest yield of scintillation light per energy unit of an incoming gamma photon and good energy resolution), which are efficiently used in the UNMI design of a thick "sandwich" crystal-LC system block, are pointed out above. Since we increased the crystal thickness to compensate for a relatively poor absorption power of NaI (due to its lower density compared to other potential scintillators), attention was paid to the absorption effects of the various practically used gamma energies in different depths of NaI. These effects are presented in Table 1, in which the total absorption fractions, A(%), of various gamma energies in different depth layers of NaI, have been computed based on the exponential attenuation law by using the following equation:

$$A(\%) = (e{-pd}^{-\mu d} - e^{-\mu dl}) * 100 \qquad (6)$$

where:
e=base of natural logarithms=2.718 . . . ;
$\mu$=linear attenuation coefficient of a particular gamma energy in NaI(TI) (cm$^{-1}$);
d=starting border of the thickness (depth) of NaI DOI layer for a gamma photon passing through it (cm); and
l=end border of the thickness (depth) of NaI DOI layer for a gamma photon passing through it (cm); for d=0, $e^{-\mu d}=1$.

| NaI (T1) Layers | Number Thickness | 1 3/8" | 2 6/8" | 1 1/4" | 2 2/4" | 3 3/4" |
|---|---|---|---|---|---|---|
| Total Attenuation A (%) | 140 KeV | 90.8 | 8.4 | 79.6 | 16.3 | 3.3 |
|  | 250 KeV | 51.1 | 25.0 | 38.0 | 23.6 | 14.6 |
|  | 360 KeV | 35.4 | 22.9 | 25.3 | 18.9 | 14.1 |
|  | 510 KeV | 27.0 | 20.0 | 19.0 | 15.5 | 12.6 |
| NaI (T1) Layers | Number Thickness | 1 1/5" | 2 2/5" | 3 3/5" | 4 4/5" | 1 1" |
| Total Attenuation A (%) | 140 KeV | 71.9 | 20.2 | 5.7 | 1.6 | 99.8 |
|  | 250 KeV | 31.7 | 21.7 | 14.8 | 10.1 | 85.1 |
|  | 360 KeV | 20.8 | 16.5 | 13.1 | 10.3 | 68.9 |
|  | 510 KeV | 15.4 | 13.1 | 11.0 | 9.3 | 56.8 |

Table 1. Total attenuation-absorption fractions of characteristic gamma photon energies in the layers of various thicknesses of NaI(T1) crystal.

Table 1 provides for a possibility to facilitate an optimum UNMI design concerning the number and thicknesses of DOI layers in a thick NaI crystal. Three different embodiments are given in Table 1 (the embodiments with one 1 in. thick layer is just comparatively shown, as it does not belong to the UNMI type of design) which can be considered from the theoretical and practical (cost) aspects:

a UNMI with
(a) two NaI layers of ⅜ in. thickness each (total thickness of ⅝ in. or 0.75 in.);
(b) three NaI layers of ¼ in. thickness each (total thickness of ¾ in. or 0.75 in.); and
(c) four NaI layers of ⅕ in. thickness each (total thickness of ⅘ in. or 0.80 in.).

As it can be seen, none of the embodiments shows (and thus, proposes) the last, deepest layer (as a supplement to the total of 1 in. thickness), since the contribution in sensitivity from this layer, for all of the gamma energies (particularly the lower ones) would be insignificantly small (relative to the increase in cost). Thus, a UNMI design with a "sandwich" type of the crystal having a total NaI thickness of 1 in. could be discarded. If we consider the fact that NaI crystal thicknesses manufactured for gamma cameras are commonly those of ⅜ in. and those of ¼ in. (for special purpose cameras, with improved spatial resolution), then the embodiment (c), with four layers of ⅕ in. thickness each, could be also discarded as a practically senseless one (an insignificant gain in spatial resolving power, negligible contribution in sensitivity even from the last two layers, and from any standpoint too expensive). Thus, two of the above-mentioned embodiments may be preferable for the UNMI design: the one with two NaI layers, each being ⅜ in. thick, and possibly the one with three NaI layers, each being ¼ in. thick. In both cases the total thickness of NaI is the same –¾ in. In addition, the embodiment with two NaI layers, each layer being ⅜ in. thick, as given in FIGS. 1, 2, and 7, may be the more preferable of these two embodiments. Such an embodiment may be the simplest and the cheapest, because: it includes the smallest number of layers, it allows easy fabrication of the block of a "sandwich" type of crystal; it includes a reduced number of UNMI PM tubes, of ADCs, as well as of fiber optics; the NaI cuts of ⅜ in. thickness are in routine production; a UNMI PM tubes array of only eight 2 in. PM tubes matches the conventional position sensitive 3 in. PM tubes array and crystal block size in a way that it can fit the existing housings and shieldings routinely produced for matched sizes of large field of view rectangular GSC heads, as given in FIG. 2; it would not be necessary to use a centroid algorithm for electronic determination of DOI, but simply, an electronic separator of the two DOI signals to select the one with greater output value). The two-crystal (⅜ in. each) embodiment may also be the most important form the standpoint of performance parameters for single photon emitters from an NaI layer (cut) of ⅜ in. thickness in conventional GSCs, such as resolution, sensitivity, are widely accepted as the optimal ones in both planar and SPECT studies.

If the Table 1 is considered analytically, the following known facts arise as significant for the UNMI design. Low energies (140 KeV and less) will be predominantly absorbed in the lower NaI layer, and with rising energy, the fractions absorbed in both layers become less different. Thus, as far as the single photon emitters are concerned, a practically important fact is that, for the energies up to 140 KeV, almost only the lower (shallow) crystal layer is efficient, and both layers become more significantly efficient just for the energies of 250 KeV and 360 KeV. On the other hand, both crystal layers are almost equally efficient for positron emitters.

Some additional facts connected with UNMI design should be also mentioned. "Intrinsic" resolution of an imaging system of the GSC type, i.e., one without the influence of a lead collimator, essentially depends on two factors: 1) the type of interaction for a gamma photon in a crystal, and 2) the statistical fluctuations of scintillation light distribution in PM tubes system. Gamma photons of the energies used in nuclear medicine mostly interact in the crystal by one of the two effects: photoelectric and Compton. Photoelectric effect is more desirable providing, in principle, for better intrinsic resolution than the Compton scatter. The probability for Compton effect increases with the increase of gamma photon energy and with the depth of absorption—interaction in a crystal, i.e., with crystal thickness. Still, it has been shown that a significantly unfavorable effect of the Compton scatter on intrinsic resolution starts with NaI crystal thicknesses of 1 in. and greater. It is also one of the reasons why only 0.75 in. has been suggested for a total NaI crystal thickness (of both layers) in UNMI design.

Statistical fluctuations in the distribution of light between PM tubes is a factor of greater influence on intrinsic resolution. The factor is dependent on both crystal thickness and gamma photon energy; intrinsic resolution becomes worse with the increase of crystal thickness and with the decrease of gamma photon energy. This factor should be less unfavorable with the gamma photons being absorbed in a deeper upper crystal layer, mostly originating from higher energy emitters. In standard GSCs with an NaI crystal thickness of ⅜ in., the distribution of light is corrected by the insertion of a non-scintillating light guide material toward PMT tubes, which is usually 0.5 in. thick. In the UNMI design, in the case when only the lower NaI layer is kept "active", such a light guide thickness is achieved by the combined thicknesses of the upper NaI layer and the light guide, coupling it optically to the conventional PM tubes array. Another possible solution for such a case is that the upper NaI layer can be optically coupled to the conventional PM tubes array only by a thin quartz layer, having the same thickness as the other two quartz layers incorporated in a "sandwich" design of the crystal-internal light collimators block. In that case, the upper NaI crystal layer itself would practically serve as a light guide for the lower NaI layer.

Figure 6:
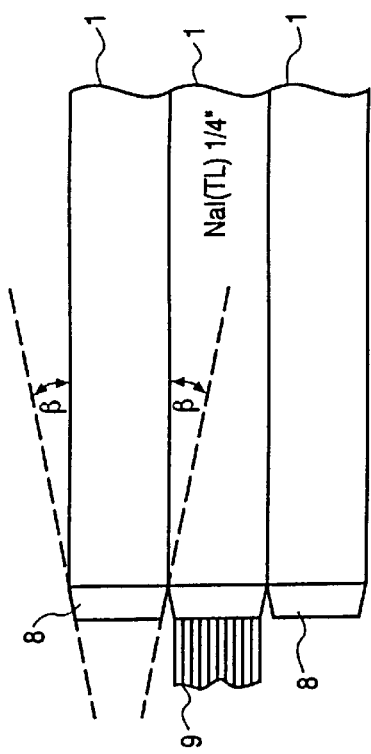
FIG. 6 illustrates, in vertical cross-section, an embodiment of an UNMI which has slopes narrowing the light collimators (LCs) in the direction from the crystal toward the fiber optics.

The suggested two embodiments of the UNMI design (2×⅜ in. and 3×¼ in. of NaI layers) would also differ in the design of external LCs. The proposed embodiment (b), 3×¼ in., as roughly shown in FIG. 6, would have slopes narrowing the LCs (in vertical cross-section) in the direction from the crystal toward the fiber optics, determined by the "critical" angle, β. The proposed embodiment (a) 2×⅜ in., which is shown in FIGS. 1 and 2 in details, and schematically shown in FIG. 7, would have different slopes for the external LCs. The slopes on the sides towards the neighboring NaI layer would also be determined by the "critical" angle, β; the slopes on the opposite sides of external LCs, i.e., towards the lead collimator and the conventional PM tubes array would be given, relative to horizontal borders of layers, by the angle: 45°-β. Thus, an angle of 45° would make a 90° angle at such a slope, with the opposite side slope of external LC being determined by the angle, β. Since these slopes have to be reflective in order to collect and shift as many as possible of the light photons towards the fiber optics (and further towards UNMI PM tubes), a slope angled, 45°-β, would prevent many of the undesired light photons from entering from the neighboring NaI layer at angles greater than, β, to be shifted towards fiber optics, reflecting them from this slope to the opposite slope angled, β, and then "back" towards the NaI layer.

Figure 8:
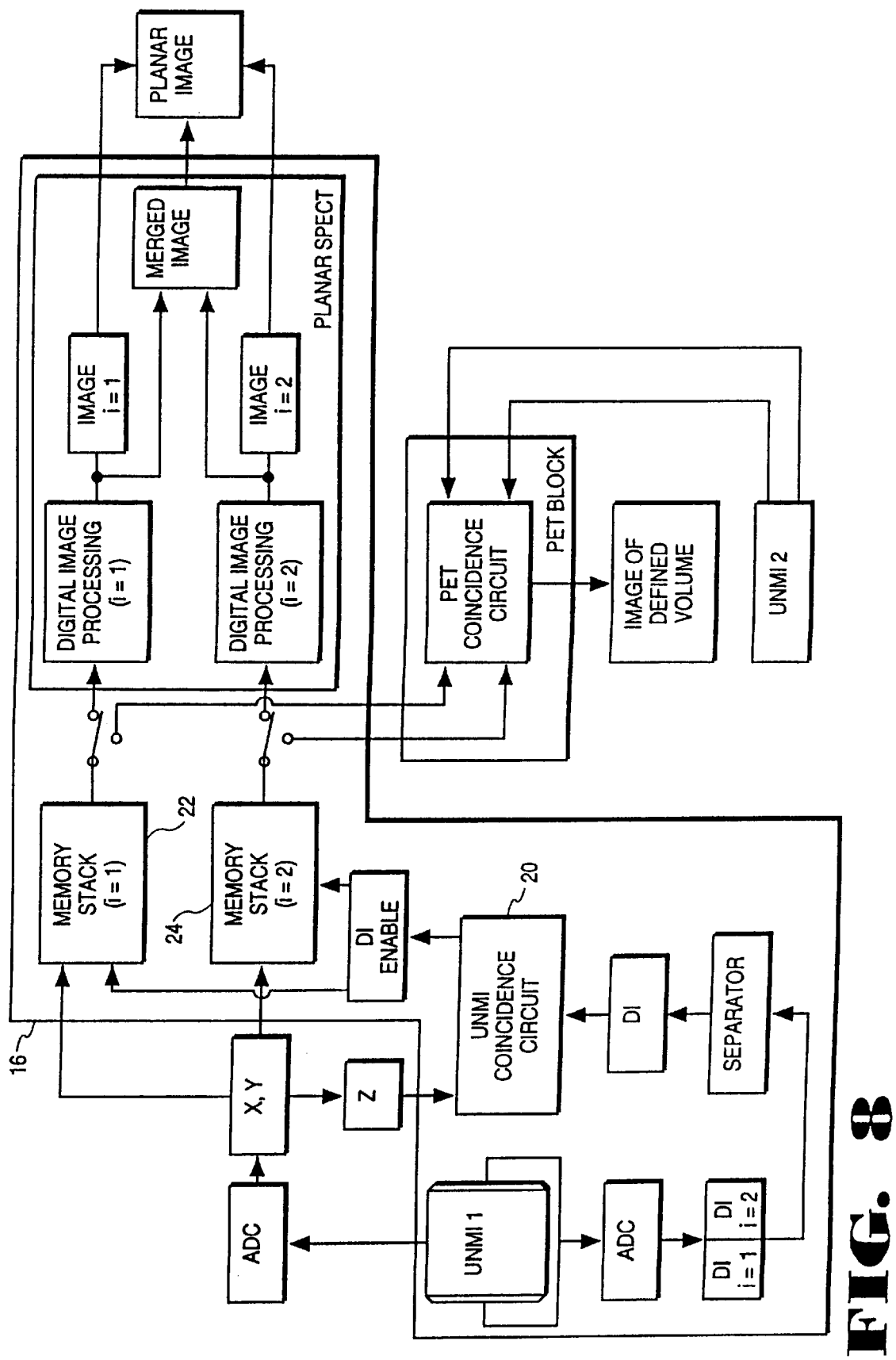
FIG. 8 is a block diagram of the UNMI's electronics.

FIG. 8 illustrates a block diagram of UNMI electronics (16), which is added to the conventional electronics of position sensitive (PS) area detectors (serving to obtain the two-dimensional (x,y) location of an IGP). The summing signal Z from the PS electronics in the UNMI detector is, by the UNMI coincidence circuit 20, put in coincidence with the signal coming from a DOI layer (in which an IGP has occurred), as determined by the UNMI electronics (obtained by the electronic comparator in a UNMI with two DOI crystal layers), to deposit the (x,y) address in one of two DOI memory stacks (22, 24) (available for each of the DOI layers). In the planar—SPECT version, upon the acquisition, the raw data from only one memory stack (coming from lower crystal layer, for the energies up to 140 KeV) or from both memory stacks (coming from both crystal layers for the energies up to 250, 360 KeV) are adequately digitally processed and filtered and are displayed as a planar image (or a SPECT projection) with an appropriately optimal resolution. The processed data can be displayed from only one DOI layer, or it can be "mixed", i.e., summed from both DOI layers of one UNMI detector (adequate digital processing and filtering protocols to be evaluated upon the system fabrication).

In the PET version, i.e., a dual UNMI detector system, located events (raw data from both memory stacks, both DOI layers) of one UNMI detector are put in coincidence by the PET coincidence circuit with the located events from memory stacks of the other oppositely positioned UNMI detector. Each memory stack (representing a particular DOI crystal layer) of one UNMI detector is in coincidence with each of the memory stacks of the other UNMI detector. It is, thus, assured that after an annihilation emission of "dual" gamma photons, the addresses from the "struck" DOI layers of both UNMI detectors, as properly located, are appropriately used in a 3D reconstruction of a PET image; the source of "parallax" error is almost completely eliminated by this and an organ volume with positron emitters is directly imaged with an enhanced resolution.

As far as the possible use of scintillation crystals other than NaI(Tl) in UNMI design is concerned, there might be of interest one that has been relatively recently published, lutetium oxyorthosilicate (LSO). LSO has certain favorable characteristics, i.e., greater density (7.4 g/cml) and shorter decay time compared to NaI, but it also has a smaller scintillation light yield than Na. Also, an unfavorable characteristic is its natural radioactivity. See E. Devitsin et al.: IEEE Trans. Nucl. Sci., 42, 4, 328 (1995).

Function of the UNMI System

Figure 7:
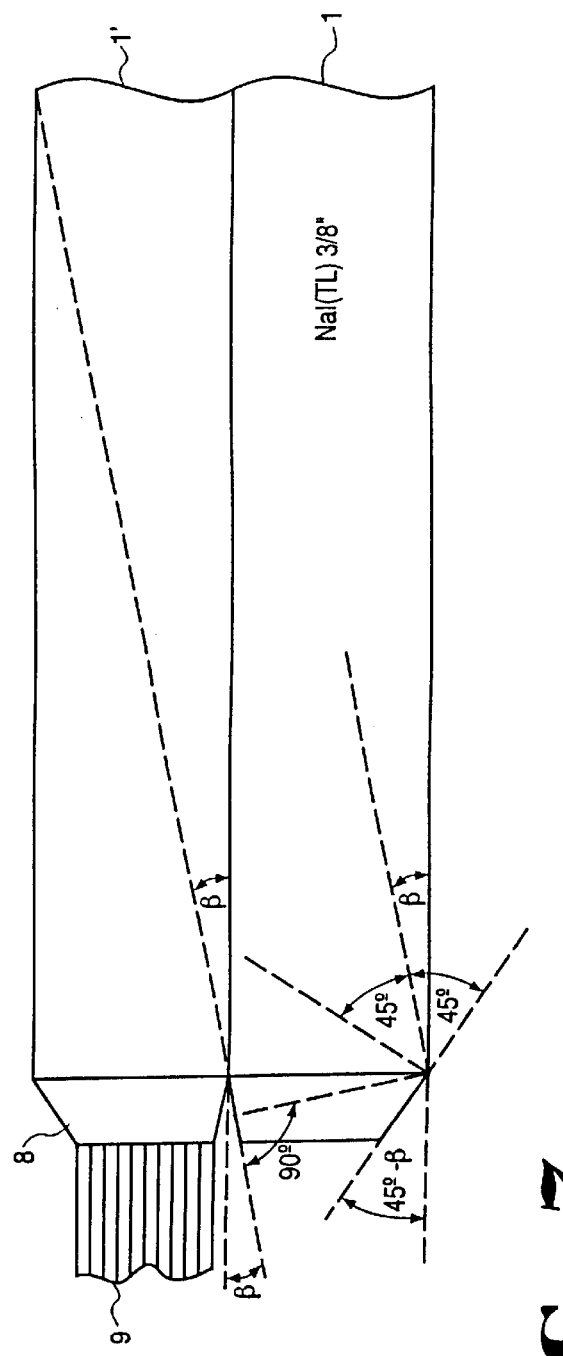
FIG. 7 illustrates schematically the UNMI design of FIGS. 1 and 2.

The design solution shown in FIGS. 1 and 2, and partially in FIG. 7, as the UNMI system, i.e., as a universal nuclear medicine imaging device, thus, functions in both modalities proposed, i.e., as a planar SPECT system for imaging the single photon gamma emitters and as a PET system for imaging the positron emitters.

UNMI as a Planar—SPECT System

Gamma photons coming from an object being imaged are absorbed in one of the two NaI(Tl) crystal layers (1, 1', in FIG. 1) after having passed through the holes of a lead collimator (6, in FIG. 1), (usually through a collimator with parallel holes—septa, as shown in proportionally drawn details in FIG. 1). No matter whether a photoelectric or a Compton effect has occurred, the absorbed gamma photons are recorded within a predetermined energy "photopeak". A number of scintillation light photons (as a function of absorbed gamma photon energy) are isotropically spread out, being "captured" by both PM tubes arrays, i.e., by the PS array (5) (for determining the 2D (x,y) location of IGP), and by the UNMI array (7) (via LC system, for determining DOI) according to the geometric efficiencies considered above and shown in FIGS. 4 and 5. Since the signals coming from both PM tubes arrays originate from the absorption of the same gamma photon, the two signals are put in coincidence by the UNMI coincidence circuit 20 within an adequate coincidence time "window". Depending on a DOI location of the absorbed gamma photon, the two-dimensional, (x,y) address is deposited in a particular memory stack available for that DOI.

Thus, the digital UNMI images originating from one, or two (or three, depending on the imager design) DOI crystal layers can be separately displayed. A display from only the lower (shallow) layer (in the proposed design with two crystal layers) can be used for energies up to 140 KeV, while keeping the upper (deep) crystal layer electronically inactive, because these energies are almost completely absorbed in the lower layer; as a result, light photons directed towards the PS PM tubes array (5) pass the upper layer, serving only as a (favorable) light guide in this case. The thickness of the upper crystal layer of ⅜ in. (0.375 in.) makes a total thickness of 0.5 in. together with the UNMI light guides (2,4), which equals the usual light guide thickness in conventional GSCs. However, gamma energies ranging 250 and 360 KeV can be imaged using both DOI crystal layers. Here, the UNMI system would be particularly advantageous, since the images acquired and stored in separate DOI memory stacks could be separately processed in a specific way. Namely, it can be supposed that the same images from two DOI layers will differ according to their essential characteristics (in particular, so far as the "intrinsic" spatial resolution represented by the "full with at half maximum" (FWHM) parameter, is concerned). In a physical experiment, the line spread function (LSF, with its FWHM parameter, can be obtained for each of the crystal layers (and each specific energy and lead collimator), and from LSF the "modulation transfer function" (MTF). MTF, being a Fourier transform of LSF, enables the obtaining of the characteristics in the frequency domain as a function of real space (i.e., obtaining the data in Fourier space); then, the use of digital filters incorporating the inverse MTF (Metz, Wiener) will be made possible, enabling "cutting" the frequency spectrum at an appropriately selected Nyquist "cut-off" frequency. Thus, it might be possible to choose an appropriate cut-off frequency for both DOI layers and achieve the same "intrinsic" resolving power for the whole depth—thickness, including both DOI layers of the crystal (for a particular energy), with the advantage that the sensitivity, as used from an integral whole of the two DOI layers of the crystal, will be maximally enhanced. So, the usefulness of digital filters in optimizing the images obtained from the total crystal thickness might be expected when using the medium single photon gamma energy ranges.

When using only one, lower DOI crystal layer for the detection of energies up to 140 KeV, it might be quite possible to use the standard, low energy lead collimators, as routinely done with conventional GSCs. When detecting the gamma energies ranging 250 and 360 KeV by using both DOI crystal layers ⅝ in. thick in total, it might be necessary to modify the medium energy (up to 360 KeV) lead collimators. It might be necessary to lengthen them in order to maintain the system resolving power but not so much as to lose the gain in sensitivity, due to increased crystal thickness, because of a negative effect of the "inverse square law".

UNMI as a PET System

Figure 9:
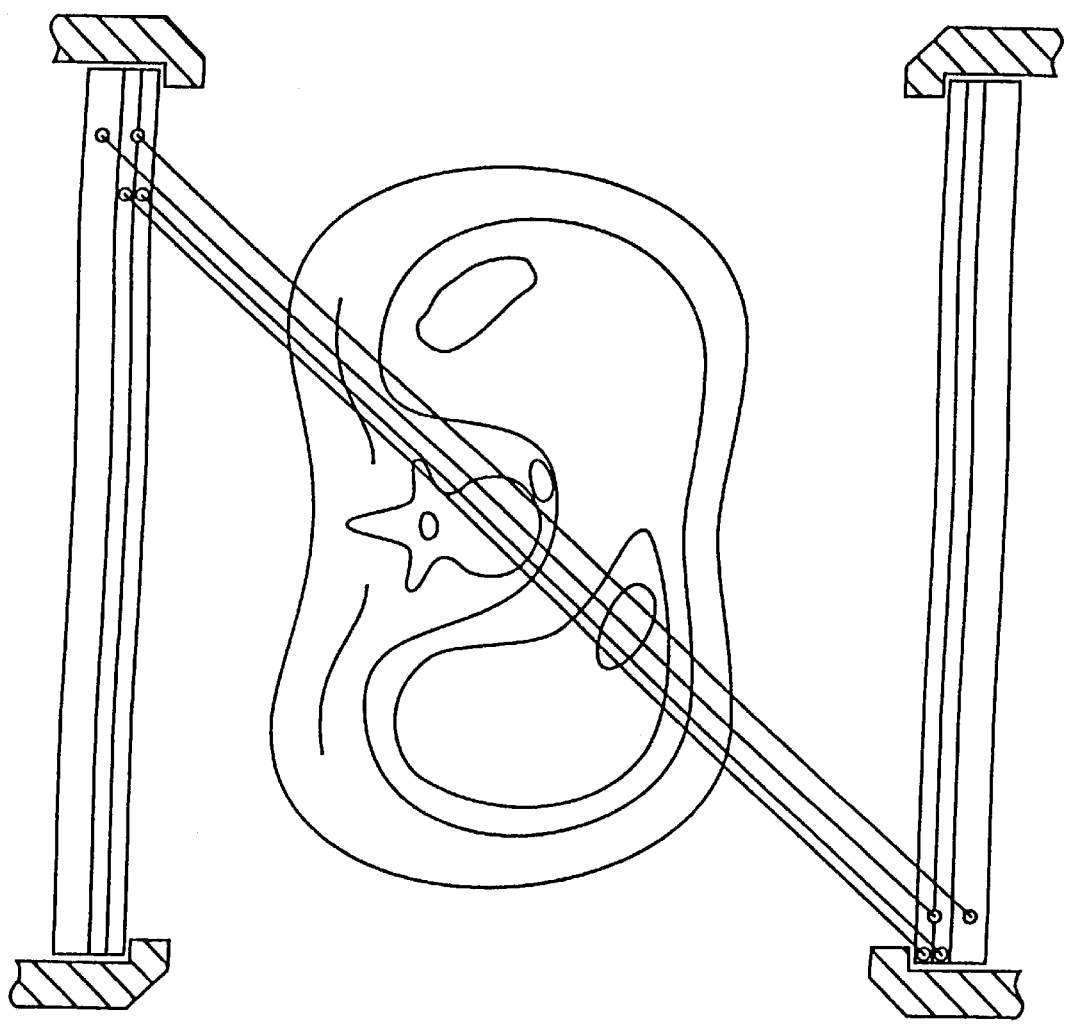
FIG. 9 is a diagram which illustrates the significance and influence of parallax error.

From Table 1, it follows that both DOI layers of the proposed UNMI embodiment with two NaI ⅜ in. thicknesses are almost equally efficient for the absorption of photon energies of 511 KeV, originating from positron emitters. Thus, the identification of a DOI layer in which the absorption takes place becomes very important, because it will get the same two-dimensional (x,y) location address. The unknown depth location, by the same two-dimensional address, leads to the "parallax error", thereby deteriorating the resolving power of the system. It has been pointed out above in the "Background of the Invention" that such an error, in a PS area detector system fitted with thick (1 in.) NaI crystals to serve as a PET machine, has been recognized as a significant factor preventing better resolving power. The significance and influence of a "parallax error" is illustrated in FIG. 9, proportionally showing the sizes of a two-detector UNMI system and of a human body cross-section at the liver level.

The possibility for an erroneous location of a positron emission due to parallax is apparent if a correct DOI were not known; that is, both of the shown positron's photon "links" are possible between the two detectors which, as evident, cause an error up to approximately one centimeter in locating the proper positron emission. The known DOI within an (x,y) address corrects for such an error and significantly improves resolving power of the UNMI PET system.

Technically, PET would be done with two opposing UNMI detectors, without lead collimators; electronically, a necessary prerequisite would be a coincident connection within one UNMI detector for DOI determination, as well as a coincident connection between each of the DOI layers of the two UNMI detectors for the detection of positron annihilation in situ (with its direct location within a defined volume of an organ), with improved spatial resolution (due to correction for parallax error).

Production/Fabrication of the UNMI

Fabrication of some of the specific parts (e.g., LC system fiber optic light cables) as well as the production technology for implementing the overall UNMI design, would be almost exclusively made possible, or at least would be made efficient and economically productive, by a relatively small number of international corporations dealing with the production of high technology imaging systems for nuclear medicine, primarily those dealing with the production of GSCs, such as ADAC Laboratories. The simplest way would be if the already-made NaI(Tl) large field of view crystals of standard 2D sizes and standard thicknesses (⅜ in.), as routinely produced for contemporary GSCs (1, in FIGS. 1 and 2), were optically coupled (a known procedure, using silicone grease) via the UNMI LC system (2, 3, 4 and 8 in FIG. 1), to form the UNMI detector block, with added fiber optics and light guides (9, 10, in FIG. 1). The specific UNMI coincidence electronics is to be added to these, made of routinely produced parts (e.g., PM tubes, digital electronic circuits), besides the also routinely produced PM tubes of standard sizes (3 in., 2 in.) and digital electronics for the 2D location of IGPs. Such a UNMI detector, fitted with standard, or slightly modified lead collimators (for planar—SPECT studies), and incorporated in almost standard mechanical parts/gantries to be moved in adequate directions, might be used for both planar and tomographic (SPECT and PET) studies.

A system with one UNMI detector and lead collimator(s) on might serve for planar static and dynamic as well as for SPECT studies. A system with two UNMI detectors with lead collimators on would serve as an efficient SPECT system, both for the "low" gamma energies up to 140 KeV (which is the chief goal of the existing SPECT systems) and as a particularly useful system for imaging the "medium" gamma energies of 250 and 360 KeV. These systems, by making use of only one of the two detectors, might be also used for planar static and dynamic studies.

The same system with two UNMI detectors in coincident electronic mode and without lead collimators, would serve as a PET system. Compared to the similar existing PET systems, its advantages would be improved spatial resolution and large angle of acceptance (due to the corrected parallax error), enabling the direct optimized 3D imaging of the particular body volumes in a quantitative functional mode. Four of the UNMI detectors might be also used in a UNMI PET system, out of which: a) two opposite detectors would be in coincidence mode, or, b) each of the detectors would be in coincidence with the remaining three ones (enabled by the large "angle of acceptance"), thus making the system maximally efficient.

So far as the technical solution for a mechanical stand—gantry and system is concerned, by means of which the UNMI detectors could be moved in appropriate directions during planar static—dynamic studies, and stable in rotational moves during tomographic studies, probably the closest to optimal solution would be the one made by ADAC Laboratories for their dual—head SPECT system.

Thus, a universal nuclear medicine imaging detector has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A radiation detector comprising:
   a plurality of scintillation layers;
   a light guide disposed between the plurality of scintillation layers to transfer light between the scintillation layers;
   a first plurality of light detection devices; and
   a plurality of light guides external to the plurality of scintillation layers and separately coupled optically to the plurality of scintillation layers and to particular ones of the first plurality of light detection devices.

2. A radiation detector as recited in claim 1, further comprising circuitry coupled to the light collimator system to determine a depth of interaction of a scintillation event in one of the scintillation layers based on output of the plurality of light guides.

3. A radiation detector as recited in claim 1, further comprising a second plurality of light detection devices optically coupled to all of the scintillation layers and located proximate a top surface of one of the scintillatoin layers.

4. A radiation detector as recited in claim 3, further comprising:
   first circuitry coupled to the light collimator system to determine a depth of interaction of a scintillation event in one of the scintillation layers based on output of the plurality of light guides; and
   second circuitry coupled to the second plurality of light detection devices to determine two-dimensional coordinates of the scintillation event.

5. A radiation detector as recited in claim 1, wherein the plurality of light guides comprises a plurality of fiber optic light guides.

6. A radiation detector as recited in claim 1, wherein each of the scintillation layers is optically coupled to a different subset of said plurality of light detection devices, wherein each said subset is mutually exclusive of every other said subset.

7. A radiation detector as recited in claim 1, wherein each of the plurality of light guides is optically coupled to an edge of one of the scintillation layers by a light collimator.

8. A gamma camera detector comprising:
   a plurality of light-sensitive devices;
   a multi-layered scintillation crystal separated into layers by at least one substantially flat light guide to transfer light between layers; and
   a light collimation system including a plurality of fiber optic light guides optically coupled to edges of the individual layers of the scintillation crystal by light collimators and optically coupled to particular ones of the light-sensitive devices, to enable determinations of depth of interaction of scintillation events in the scintillation crystal layers based on output of the plurality of light guides.

9. A gamma camera detector as recited in claim 8, further comprising:
   means for determining two-dimensional coordinates of the scintillation event; and
   means for determining a depth of interaction of the scintillation event based on output of the plurality of light guides.

10. A radiation detector of a medical imaging system, the radiation detector comprising:
    a plurality of scintillation crystal layers;
    a first plurality of light detection devices;
    a second plurality of light detection devices optically coupled to each of the scintillation crystal layers;
    a plurality of light guides to optically couple each of the plurality of scintillation crystal layers to a different subset of the first plurality of light detection devices, such that each said subset is mutually exclusive of each other said subset.

11. A radiation detector as recited in claim 10, further comprising a substantially flat light guide disposed between two of the layers to transfer light between said two of the layers.

12. A radiation detector as recited in claim 10, further comprising:
    first circuitry to compute a depth of interaction of a scintillation event in said one of the scintillation crystal layers based on output of one or more of the first plurality of light detection devices; and
    second circuitry to compute x-y coordinates of a scintillation event in one of the scintillation crystal layers based on output of one or more of the second plurality of light detection devices.

13. A radiation detector for a medical imaging system, the radiation detector comprising:
    a plurality of substantially flat scintillation crystal layers optically coupled to each other and disposed in a stacked configuration, each of the scintillation crystal layers having two substantially parallel large surfaces and plurality of edges, the stacked configuration oriented in the detector to allow gamma rays from an object of interest to impinge on a large surface of each scintillation crystal layer;
    a first plurality of light detection devices;
    a light collimator system including a plurality of sets of light guides, each set of light guides optically coupled to a corresponding one of the scintillation crystal layers by a light collimator and to a corresponding subset of the first plurality of light detection devices, each set of light guides having an input end located proximate an edge of the corresponding scintillation crystal layer and an output end located proximate the corresponding subset of the first plurality of light detection devices; and
    a second plurality of light detection devices located proximate a large surface of a top one of the scintillation crystal layers and optically coupled to all of the scintillation crystal layers.

14. A radiation detector as recited in claim 13, further comprising a substantially flat light guide disposed between two of the layers.

15. A radiation detector as recited in claim 13, further comprising first circuitry to compute a depth of interaction of a scintillation event in one of the layers based on output of one of the subsets of the first plurality of light detection devices.

16. A radiation detector as recited in claim 15, further comprising second circuitry to compute x-y coordinates of a scintillation event in one of the layers based on output of one or more of the second plurality of light detection devices.

17. A radiation detector for a medical imaging system, the radiation detector comprising:

a plurality of substantially flat scintillation crystal layers optically coupled to each other and disposed in a stacked configuration, each of the layers having two substantially parallel large surfaces and a plurality of edges, the stacked configuration oriented to allow gamma rays from an object of interest to impinge on a large surface of each layer;

a substantially flat light guide disposed between two of the layers to transfer light between said two of the layers;

a first plurality of light detection devices;

a light collimator system including a plurality of sets of light guides to enable a depth of interaction determination, each set of light guides including a fiber optic transmission medium, each set of light guides optically coupled to a corresponding one of the layers and to a corresponding subset of the first plurality of light detection devices, each set of light guides having an input end located proximate an edge of the corresponding layer and an output end located proximate the corresponding subset of the first plurality of light detection devices;

a second plurality of light detection devices located proximate a large surface of one of the layers and optically coupled to all of the layers;

first circuitry to compute a depth of interaction of a scintillation event in one of the layers based on output of one of the subsets of the first plurality of light detection devices; and second circuitry to compute x-y coordinates of a scintillation event in one of the layers based on output of one or more of the second plurality of light detection devices.

18. A gamma camera imaging system capable of use in either a single-photon emission computed tomography (SPECT) mode or a positron emission tomography (PET) mode, the imaging system comprising:

a plurality of radiation detectors, each of the detectors including
      a plurality of scintillation crystal layers,
      at least one light guide to transfer light between the scintillation crystal layers, each said at least one light guide disposed between two of the plurality of scintillation crystal layers,
      a first set of light detection device for use in depth of interaction (DOI) determinations, and
      a second set of light detection devices including a two-dimensionally position sensitive array of light devices optically coupled to all of the plurality of scintillation crystal layers;
      a plurality of sets of light guides external to the plurality of scintillation layers and separately couple optically to the plurality of scintillation crystal layers and to particular ones of the first set of light detection devices, the plurality of sets of light guides including fiber optic light transmission media; and a processing system to process signals corresponding to interactions of gamma photons (IGPs), the processing system including
      a plurality of analog-to-digital converters to convert analog signals output from the light detection devices into digital signals,
      a first set of memory stacks,
      a first coincidence circuit connecting a signal of a two-dimensional location of an IGP and a DOI signal to store the two-dimensional locations of the IGPs in the first set of memory stacks as raw data based on the number of scintillation crystal layers in which the DOI is to be determined,
      a second set of memory stacks to store digitally processed images, the number of which corresponds in the SPECT mode to a number of raw image stacks, wherein data from one or more of the first and second sets of stacks can be used to generate displayable images, and
      a second coincidence circuit to connects each of the memory stacks having the raw data of the first detector to the memory stacks having the raw data of the second detector for using the determined DOIs while in the PET mode.

19. A gamma camera imaging system as recited in claim 18, wherein the scintillation crystal layers are substantially flat, optically coupled to each other, and disposed in a stacked configuration, each of the layers having a plurality of substantially parallel large surfaces and a plurality of edges, the stacked configuration oriented to allow gamma rays from an object of interest to impinge on a large surface of each layer; and wherein each of the sets of light guides is optically coupled to a corresponding one of the scintillation crystal layers and to a corresponding subset of the first set of light detection devices, each set of light guides having an input end located proximate an edge of the corresponding scintillation crystal layer and an output end located proximate the corresponding subset of the first set of light detection devices.

* * * * *